United States Patent [19]

Fisher et al.

[11] 4,212,880

[45] Jul. 15, 1980

[54] SYMMETRICALLY SUBSTITUTED PYROMELLITIC DIIMIDES AS RUMINANT FEED ADDITIVES

[75] Inventors: Michael H. Fisher, Bridgewater; Peter Kulsa, Plainfield; Bruce O. Linn, Bridgewater, all of N.J.

[73] Assignee: Merck & Co., Inc., Rahway, N.J.

[21] Appl. No.: 954,039

[22] Filed: Oct. 23, 1978

[51] Int. Cl.$^2$ .............................................. A61K 31/40
[52] U.S. Cl. ..................................................... 424/274
[58] Field of Search ......................................... 424/274

[56] References Cited

U.S. PATENT DOCUMENTS

| | | | |
|---|---|---|---|
| 2,776,889 | 1/1957 | Standen | 424/274 |
| 3,624,212 | 11/1971 | Hennart | 424/273 |
| 3,738,840 | 6/1973 | Anderson | 96/100 |

FOREIGN PATENT DOCUMENTS

| | | |
|---|---|---|
| 1004675 | 9/1965 | United Kingdom . |
| 1157503 | 7/1969 | United Kingdom . |
| 1173943 | 12/1969 | United Kingdom . |
| 1181020 | 2/1970 | United Kingdom . |

OTHER PUBLICATIONS

*Zhurnal Organicheshoi Khimii*, (1966), vol. 2, No. 7, pp. 1265–1267.
*Chemical Abstracts*, vol. 84:135046 (1975); vol. 76, 72279q, 33987x (1972); vol. 59, 372c (1963); vol. 84, 150376a (1976); 84, 43982y (1976); 83:59699b (1975); 82:87103a (1975); 79:19700f (1973); 77:48850u (1972); 75:89332d (1971); 75:63340e (1971); 74:55134m (1971); 71:81122g (1969); 71:61062j (1969); 70:38694n (1969); 69:97581a (1968); 69:43899s (1968); 68:59326t (1968); 68:59329w; 67:116726d (1967); 65:13620f (1966); 63:4435f (1965); vol. 60:4054g (1964).

*Primary Examiner*—Frederick E. Waddell
*Attorney, Agent, or Firm*—David L. Rose; Harry E. Westlake

[57] ABSTRACT

Symmetrically substituted pyromellic diimides are disclosed wherein the compounds are substituted with a variety of substituent groups. The symmetrically substituted compounds are useful for administration to ruminant animals to increase feed efficiency, shift volatile fatty acid production in the ruminant from acetate with an increase in the more energetically efficient propionate and butyrate and to suppress methane formation in the rumen. Compositions and methods of treatment utilizing said compounds as the active ingredient thereof are also disclosed.

15 Claims, No Drawings

SYMMETRICALLY SUBSTITUTED PYROMELLITIC DIIMIDES AS RUMINANT FEED ADDITIVES

SUMMARY OF THE INVENTION

The compounds of this invention are described as symmetrically substituted pyromellitic diimides wherein the substitution is on the two imide nitrogen atoms. Such compounds are useful as feed additives for ruminants. Thus, it is an object of this invention to describe such compounds. A further object of this invention is to describe processes for the preparation of such compounds. A still further object is to describe the use of such compounds for the administration to ruminant animals in order to increase feed efficiency, to shift the production of volatile fatty acids away from acetate with an increase in propionate and butyrate, and to suppress methane formation. Further objects will become apparent from a reading of the following description

DESCRIPTION OF THE INVENTION

The symmetrically substituted pyromellitic diimides of this invention are best described in the following structural formula:

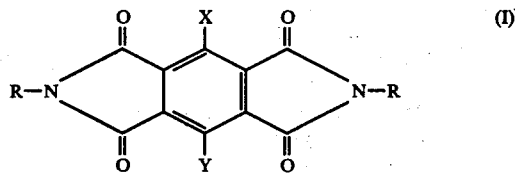

wherein each R is the same and represents hydrogen, loweralkyl, loweralkenyl, loweralkynyl, cyclopropyl nitrophenyl, substituted loweralkyl wherein the substituent is one or two of hydroxy, hydroxyloweralkoxy, hydroxyloweralkylthio, amino, mono- or di-loweralkyl amino, mono- or di-(hydroxy substituted loweralkyl) amino, loweralkanoyloxy, loweralkoxy, mercapto, loweralkylthio, loweralkylsulfinyl, loweralkylsulfonyl or loweralkoxycarbonyl; loweralkanoyl, benzoyl, diloweralkylamino or mono-substituted amino wherein the substituent is loweralkanoyl, benzoyl or loweralkanoyloxy; X and Y are independently hydrogen, halogen or loweralkyl.

In the instant application the term "loweralkyl" is intended to include those alkyl groups containing from 1 to 3 carbon atoms in either a straight or branched configuration. Exemplary of such alkyl groups are a methyl, ethyl, propyl, isopropyl, and the like.

The term "loweralkenyl" is intended to include those alkenyl groups containing a single unsaturation in a straight or branched chain length of from 2 to 6 carbon atoms. Exemplary are the groups ethenyl, propenyl, butenyl, pentenyl, hexenyl and the like.

The term "loweralkanoyl" is intended to include those alkanoyl groups of straight or branched configuration containing from 2 to 6 carbon atoms exemplified by acetyl, propionyl, butyryl, isobutyryl, pentanoyl, hexanoyl and the like.

The term "loweralkanoyloxy" is intended to include the foregoing loweralkanoyl groups bonded to the substrate through an oxygen atom.

The term "loweralkoxy" is intended to include those alkoxy groups containing from 1 to 6 carbon atoms in either a straight or branched configuration, exemplified by methoxy, ethoxy, propoxy, isopropoxy, butoxy, tert-butoxy, pentoxy, hexoxy and the like.

The preferred compounds of this invention are realized in the foregoing structural formula wherein R is hydrogen, loweralkyl, loweralkenyl, substituted loweralkyl wherein the substituent are one or two of hydroxy, amino, mono- or di-loweralkylamino, hydroxyloweralkoxy, hydroxyloweralkylthio, loweralkanoyloxy, loweralkoxy or loweralkoxycarbonyl; loweralkanoyl, di-loweralkyl amino, or loweralkanoylamino.

More preferred compounds of this invention are realized when R is the above formula is hydrogen, loweralkyl, loweralkenyl, substituted loweralkyl wherein the substituent is one of hydroxy or loweralkanoyloxy; loweralkanoyl or diloweralkylamino.

The most preferred compounds of this invention are those where R is hydrogen or hydroxyloweralkyl.

The compounds of this invention are prepared by processes outlined in the following reaction scheme:

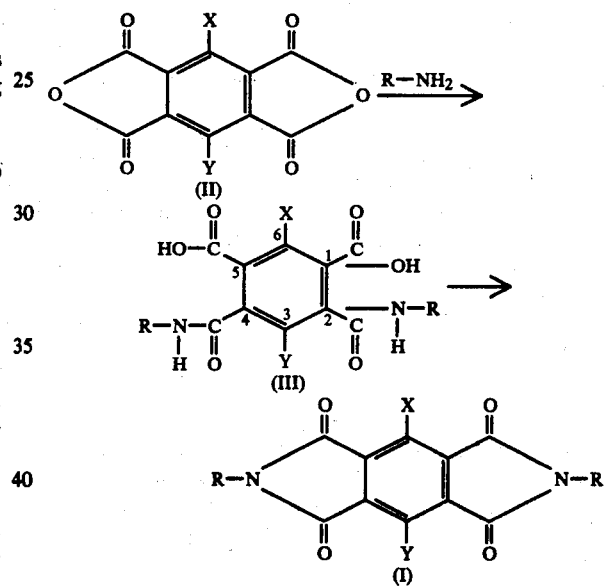

wherein R, X and Y are as defined above.

The process for the preparation of the instant compounds begins with pyromellitic dianhydride (II), a known compound, which is treated with ammonia or an R substituted amine. The reaction is carried out in an aprotic solvent such as acetone, tetrahydrofuran, dimethylformamide, dioxane, and the like. The reaction is complete in about 5 minutes to 2 hours at a temperature of from 0° C. to RT. Two moles of the amine is employed for each mole of pyromellitic dianhydride which is being reacted. The reaction is preferably maintained in an anhydrous state and anhydrous amines are preferably employed, since water will react with the anhydride at longer reaction times (greater than 2 hours). It is not generally necessary to isolate intermediate (III) and the following heating step may be carried out on the first reaction mixture directly, if the solvent is suitable or solvent may merely be removed and substituted with a second step solvent.

The product (III) which is produced is actually a mixture of isomers, since the two anhydride rings of pyromellitic dianhydride need not open up in the same manner. No attempt is made to separate the isomers, however, since the ring closure reaction will yield the same product (I) from either isomer. The mixture of isomers of benzene 1,4-dicarboxylic acid 2,5-diamide and benzene 1,5-dicarboxylic acid 3,4-diamide is heated to form the pyromellitic diimide compounds of this invention. The heating may take place in refluxing thionyl chloride and is complete in about 1-10 hours. No solvent is employed when the intermediate is heated in thionyl chloride. Alternatively the mixture of isomers may be heated in a high boiling solvent such as dimethylformamide at from about 100° C. to the reflux temperature of the reaction mixture. The reaction is complete in this case in about 178 to 1 hour. The reaction products (I) are isolated following procedures known to those skilled in this art.

Many of the compounds of this invention are conveniently prepared by reacting a substituent on the pyromellitic diimide moiety to prepare a different substituent. Such compounds are often also prepared by the above procedure, however, occasionally it is more convenient to delay the subsequent reaction until after the pyromellitic diimide compound is formed, in order to minimize side reactions, to facilitate the work-up procedures, and the like.

An example of such would be the reactions carried out on the N,N' hydroxyalkyl or aminoalkyl pyromellitic diimides. For the reactions preparing derivatives thereof, such as acyl derivatives, it is more convenient to acylate the N,N'-hydroxyalkyl or aminoalkyl compound than to use the acylated compound as starting material. While it is possible to carry out the reaction either way, the later acylation avoids the possibility that the acyl group will be removed by hydrolysis during the course of the reaction.

Such an acylation of the hydroxyalkyl, or aminoalkyl substituted pyromellitic diimide is carried out using standard acylation reagents such as the anhydride or acid halide of the acyl moiety. With lower molecular weight reagents such as acetic and propionic anhydride, the reagent is used as a solvent. For higher molecular weight reagents, where excess reagent would be more difficult to remove, an equivalent amount or a slight excess is employed and a solvent such as pyridine is employed. The reaction is carried out at from room temperature to the reflux temperature of the reaction mixture, preferably at from 75°-100° C., for from 5 minutes to 5 hours. The product is isolated using techniques known to those skilled in this art.

The compounds of the instant invention wherein the R-group contains a sulfur (thio) linkage are conveniently oxidized to the sulfinyl or sulfonyl linkages. This is carried out using mild oxidizing agents, such as m-chloroperbenzoic acid. A single molar equivalent is employed for the preparation of the sulfinyl group and two equivalents are used to prepare the sulfonyl group. The reaction is carried out in an inert solvent such as a halogenated hydrocarbon, (methylene chloride, chloroform, carbon tetrachloride, and the like), a loweralkanol or acetic acid or mixtures thereof. The reaction is complete in from 10 minutes to 10 hours. To prepare the sulfinyl compound the temperature is generally maintained at room temperature. To prepare the sulfone, temperatures up to 100° C. or the reflux temperature are employed. The products are isolated using techniques used by those skilled in the art.

The compound where R is hydroxy methyl is generally prepared by reacting pyromellitic diimide (R=H) with formaldehyde in the presence of a base such as an alkali metal hydroxide, preferably sodium hydroxide. The reaction is carried out preferably in an aqueous solvent at from room temperature to 100° C. for from 1 to 10 hours. The products are isolated using known techniques.

In the course of investigating the efficiency of feed use, the mechanism by which ruminants digest and degrade the components of their feed to form molecules which can be metabolically utilized has been intensively studied. The mechanism of carbohydrate utilization is now well known. Microorgansims in the rumen of the animal ferment the carbohydrate to produce monosaccharides and then degrade the monosaccharides to pyruvate compounds.

Pyruvate is then metabolized by microbiological processes to either acetate or propionate compounds, which may be either acids or other forms of the radicals. Two acetate radicals may be combined thereafter, still in the rumen, to form butyrates.

The animal can utilize butyrate, propionate, and acetate with differing degrees of efficiency. Utilization of these compounds which are collectively known as volatile fatty acid (VFA) occurs after absorption from the gut of the animal. Butyrate is utilized most efficiently, and acetate the least efficiently. However, the relative efficiency of use to butyrate is negated by the inefficiency of the manufacture of butyrate, which must be made from acetate in the rumen.

One of the major inefficiencies in the rumen is in the manufacture of acetate. Since it is made by the degradation of a pyruvate molecule, each molecule of acetate which is produced is accompanied by a molecule of methane. Most of the methane produced is lost through eructation. Since butyrate is made from two molecules of acetate, each molecule of the relatively efficiently used butyrate involves the loss to the animal of two molecules of methane, with all of the associated energy.

Thus, the efficiency of carbohydrate utilization (carbohydrates being the major nutritive portion of ruminant animals' feed) can be increased by treatments which encourage the animal to produce propionate rather than acetate from the carbohydrates. Further, the efficiency of feed use can be effectively monitored by observing the production and concentration of propionate compounds in the rumen. If the animal is making more propionates, it will be found to be using its feed more efficiently. This efficiency is manifested by greater weight gains per feed intake, a reduction in energy losses by methane release, and economic advantages to the animal grower when the animal is sold for consumption.

The method of improving the feed utilization of ruminants of this invention comprises orally administering to a ruminant an effective amount of one or more of the above-described novel compounds. Of course, the most economically important ruminant animals (those with multiple stomachs, one of which functions as a rumen) are cattle, sheep and goats. The compounds of this invention are administered to ruminants orally at rates of from about 0.1 mg/kg/day to about 10 mg/kg/day. While that range is functional, the preferred range of rates is from about 0.5 to 5 mg/kg/day.

It has been found that the compounds of this invention increase the efficiency of feed utilization in ruminant animals. The easiest way to administer the compounds is by mixing them in the animal's feed. However, the compounds of this invention can be usefully administered in other ways. For example, they can be incorporated into tablets, drenches, boluses, or capsules, and dosed to the animals. Formulation of the compounds in such dosage forms can be accomplished by means and methods well known in the veterinary pharmaceutical art. Each individual dosage unit should contain a quantity of the feed-efficiency-improving compound which has a direct relation to the proper daily dose for the animal to be treated.

Capsules are readily produced by filling gelatin capsules with any desired form of the desired compound. If desired, the compound can be diluted with an inert powdered diluent, such as a sugar, starch or purified crystalline cellulose, in order to increase its volume for convenience in filling capsules.

Tablets of the compounds useful in this novel method are made by conventional pharmaceutical processes. Manufacture of tablets is a well-known and highly-advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used. Commonly used absorbents again include starch and lactose, while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps, and polyethylene glycol.

This method of increasing the efficiency of feed utilization can also be practiced by the administration of the instant compound as a slow-pay-out bolus. Such boluses are made as tablets are made, except that a means to delay the dissolution of the compound is provided. Boluses are made to release for lengthy periods. The slow dissolution is assisted by choosing a highly water-insoluble form of the compound. A substance such as iron filings is added to raise the density of the bolus and keep it static on the bottom of the rumen.

Dissolution of the compound is delayed by use of a matrix of insoluble materials in which the drug is embedded. For example, substances such as vegetable waxes, purified mineral waxes, and water insoluble polymeric materials are useful.

Drenches of the instant compounds are prepared most easily by choosing a water soluble or water dispersable form of the compound. If an insoluble form is desired for some reason, a suspension may be made. Alternatively, a drench may be formulated as a solution in a physiologically acceptable solvent such as a polyethylene glycol.

Suspension of insoluble forms of the compounds can be prepared in non-solvents such as vegetable oils such as peanut, corn, or sesame oil; in a glycol such as propylene glycol or a polyethylene glycol; or in water, depending on the form of the compound chosen.

Suitable physiologically acceptable adjuvants are necessary in order to keep the compound suspended. The adjuvants can be chosen from among the thickeners, such as carboxymethylcellulose, polyvinylpyrrolidone, gelatin, and the alginates. Many classes of surfactants also will serve to suspend the compounds. For example, lecithin, alkylphenol polyethylene oxide adducts, naphthalene sulfonates, alkylbenzenesulfonates and the polyoxyethylene sorbitan esters are useful for making suspension in liquid nonsolvents.

In addition, many substances which effect the hydrophilicity, density, and surface tension of the liquid can assist in making suspensions in individual cases. For example, silicone anti-foams, glycols, sorbitol, and sugars can be useful suspending agents.

The suspendable compound may be offered to the animal grower as a suspension, or as a dry mixture of the compound and adjuvants to be diluted before use.

These compounds may also be administered in the drinking water of the ruminants. Incorporation into drinking water is performed by adding a water soluble or water suspendable form of desired compound to the water in the proper amount. Formulation of the compound for addition to drinking water follows the same principles as formulation of drenches.

The most practical way to treat animals with the compounds of this invention usable in this novel method is by the formulation of the compound into the feed supply. Any type of feed may be medicated with the instant compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about 1 to about 400 g. of drug per pound (454 g.) of premix. The wide range results from the wide range of concentration of drug which may be desired in the final feed. Premixes may be either liquid or solid.

The formulation of ruminant feeds containing the proper amounts of the instant compounds for useful treatment is mainly a matter of arithmetic. It is necessary only to calculate the amount of compound which it is desired to administer to each animal, to take into account the amount of feed per day which the animal eats, and the concentration of compound in the premix to be used, and calculate the proper concentration of the compound in the feed.

All of the methods of formulation, mixing, and pelleting feeds which are normally used in the ruminant feed art are entirely appropriate for manufacturing feeds containing the compounds usable in this method.

It is not intended that the scope of this invention be limited to any particular formulations or methods of administration. The invention is a method of increasing the efficiency of feed utilization by ruminant animals by the oral administration of certain compounds regardless of the method of administration of the compounds.

It is usual to treat economic animals, including ruminants, with a variety of growth promoters, disease preventives, and disease treatments throughout their lives. Such drugs are often used in combination. The novel method may be practiced in combination with other treatments.

EXAMPLE I

Pyromellitic Diimide

A suspension of 233 g. (0.92 mole) of pyromellitic acid in 80.0 ml. (1.96 mole) of 98% formamide and 630 ml. of 1-methyl-2-pyrrolidinone is stirred under nitrogen and heated gradually to 160° C. At about 120° C. gas evolution is observed and distillation of water and formic acid starts. Distillation is continued while heating at 160° C. for 40 minutes. On cooling, the product precipitates and is collected. The cake is rinsed with cold 1-methyl-2-pyrrolidinone, with cold methanol and with ethyl ether. After drying, 138 g. of pyrmellitic diimide is obtained. The product is further purified by recrystallization from dimethylformamide. The decomposition point at approximately 435° C. is determined by differential thermal analysis.

EXAMPLE 2

N,N'-Dimethylpyromellitic diimide

30 Ml. (0.66 mole) of liquid methylamine is bubbled into a solution containing 65.4 g. (0.30 mole) of pyromellitic dianhydride in 1.0 l. of dimethylformamide. This mixture is stirred at room temperature (23° C.) for 1 hour, at 95° C. for 1 hour, at reflux for 1 hour and then cooled in ice and diluted with 750 ml. of water. The crystals are collected, rinsed with cold dimethylformamide, cold methanol, cold ethyl ether and dried furnishing 76.5 g. of N,N'-dimethylpyromellitic diimide, m.p,. 300° C. The product is further purified by recrystallization from dimethylformamide.

EXAMPLE 3

N,N'-Diethylpyromellitic diimide

14 Ml. (0.22 mole) of anhydrous ethylamine is added to 43.6 g. (0.20 mole) of pyromellitic dianhydride in 250 ml. of dimethylformamide. The mixture is stirred at room temperature for 1 hour., at 95° C. for 1 hour and at reflux for 1 hour and then cooled in ice. The insolubles are collected, rinsed with cold dimethylformamide, cold methanol, cold ethyl ether and dried, furnishing 49.7g. of N,N'-diethylpyromellitic diimide, m.p. 274°–275° C. The product may be recrystallized from methylene chloride and hexane.

EXAMPLE 4

N,N'-Diallyl pyromellitic diimide 33.1 Ml. (0.44 mole) of allylamine is added to 43.6 g. (0.20 mole) of pyromellitic dianhydride in 300 ml. of dimethylformamide. The mixture is stirred at room temperature (23° C.) for 1 hour, at 95° C. for 1 hour, at reflux for 1 hour, and then cooled in ice and diluted with 150 ml. of water. The insolubles are collected, rinsed with cold water, cold methanol, cold ethyl ether and dried furnishing 47.0 g. of N,N'-diallyl pyromellitic diimide, m.p. 223°–224° C. The product may be recrystallized from methylene chloride and petroleum ether.

TABLE I

N,N'-symmetrically Disubstituted Pyromellitic Diimides with Hydrocarbon Side Chains Prepared as Described in Example 4

| Hydrocarbon Amine Reactant | Pyromellitic Diimide Product | M.P. °C. |
|---|---|---|
| Isopropylamine | N,N'-diisopropyl | 293–294 |
| Cyclopropylamine | N,N'-bis(cyclopropyl) | >300 |
| Propargylamine | N,N'-bis(2-propyn-1-yl) | >300 |

EXAMPLE 5

N,N'-bis(Hydroxymethyl)pyromellitic diimide

Powdered pyromellitic diimide, 30 g. (0.14 mole) is added rapidly to a solution containing 60 ml. of 36% formaldehyde in 300 ml. of water and 0.60 ml. of 2.5 N soldium hydroxide with vigorous stirring. The mixture is heated on a steam bath for 3 hours and then cooled in an ice bath. The precipitate is collected, rinsed with cold water, cold methanol, cold ethyl ether and then dried furnishing 27.8 g. of N,N'-bis(hydroxymethyl)pyromellitic diimide, m.p. 300° C.

EXAMPLE 6

N,N'-bis(2-Hydroxyethyl)pyromellitic diimide 13.2 Ml. (0.22 mole) of ethanolamine is added to a solution containing 21.8 g. (0.10 mole) of pyromellitic dianhydride in 100 ml. of dimethylformamide with stirring at room temperature (23° C.). The mixture is stirred for 15 minutes at room temperature for 1 hour at reflux, and then cooled in ice and diluted with two volumes of water. The crystals are collected, rinsed thoroughly with cold water, cold methanol and cold ethyl ether and then dried yielding 22.7 g. of N,N'-bis(2-hydroxyethyl) pyromellitic diimide, m.p. 280°–281° C. The product is recrystallized from dimethylformamide and water.

TABLE II

N,N'-Symmetrically Disubstituted Pyromellitic Diimides Containing Hydroxy in the Side Chain Prepared as Described in Example 6

| Hydroxyalkylamine Reactant | Pyromellitic Diimide Product | M.P. °C. |
|---|---|---|
| 3-Amino-1-propanol | N,N'-bis(3-hydroxyprop-1-yl) | 243–244 |
| 4-Amino-1-butanol | N,N'-bis(4-hydroxybutyl-1-yl) | 218–219.5 |
| 5-Amino-1-pentanol | N,N'-bis(5-hydroxypent-1-yl) | 208–209 |
| 6-Amino-1-hexanol | N,N'-bis(6-hydroxyhex-1-yl) | 154–155 |
| 1-Amino-2-propanol | N,N'-bis(2-hydroxyprop-1-yl) | 247.5–249 |
| 2-Amino-1-butanol | N,N'-bis(1-hydroxybut-2-yl) | 171–172 |
| 3-Amino-1,2-propanediol | N,N'-bis(2,3-dihydroxyprop-1-yl) | 277–279 |
| 2-(2-Aminoethoxy)ethanol | N,N'-bis[2-(2-hydroxyethoxy)eth-1-yl] | 193–194 |
| 2-[(2-Aminoethyl)-thio]ethanol | N,N'-bis[2-(2-hydroxyethyl)thioeth-1-yl] | 197–198.5 |
| N-(3-Aminopropyl)diethanolamine | N,N'-bis 3[di(2-hydroxyethyl)amino]prop-1-yl | 131–132.5 |

EXAMPLE 7

N,N'-bis(Acetoxymethyl)pyromellitic diimide

25 G. of N,N'-bis(hydroxymethyl) pyromellitic diimide is stirred in 300 ml. of pyridine/acetic anhydride (2:1) at room temperature (23° C.) for 4 hours and then cooled in ice. The crystals are filtered, rinsed with cold ether and dried. The product is recrystallized from methylene chloride and hexane, furnishing 12.6 g. of N,N-bis (acetoxymethyl) pyromellitic diimide, m.p. 237°–238° C.

Other acetoxy products (Table III) are prepared by heating at 95° C. for 3 hours in pyridine/acetic anhydride (1:1). If crystals do not appear on cooling, the solution is evaporated to dryness in vacuo, and the residue is crystallized from methylene chloride and hexane.

TABLE III

N,N'-Symmetically Disubstituted Pyromellitic Diimides with Acetoxy in the Side Chains Prepared as Described in Example 7

| Hydroxy Pyromellitic Diimide Reactant | Pyromellitic Diimide Product | M.P. °C. |
|---|---|---|
| N,N'-bis(2-Hydroxyethyl) | N,N'-bis(2-acetoxyethyl) | 189–190 |
| N,N'-bis(3-Hydroxyprop-1-yl) | N,N'-bis(3-acetoxyprop-1-yl) | 145–146 |
| N,N'-bis(4-Hydroxybut-1-yl) | N,N'-bis(4-acetoxybut-1-yl) | 137–138 |
| N,N'-bis(5-Hydroxypent-1-yl) | N,N'-bis(5-acetoxypent-1-yl) | 154–155 |
| N,N'-bis(2-Hydroxyprop-1-yl) | N,N'-bis(2-acetoxyprop-1-yl) | 187 |
| N,N'-bis(1-Hydroxybut-2-yl) | N,N'-bis(1-acetoxybut-2-yl) | 156–157 |
| N,N'-bis[2-(2-Hydroxyethoxy)eth-1-yl] | N,N'-bis[2-(2-acetoxyethoxy)eth-1-yl] | 97–98 |
| N,N'-bis[2-(2-Hydroxyethyl)thioeth-1-yl] | N,N'-bis[2(2-acetoxyethyl)thioeth-1-yl] | 123–124 |

TABLE IV

Other N,N'-Symmetrically Disubstituted Pyromellitic Diimides Containing Substituted Alkyl or Phenyl Side Chains Prepared as described in Example 6

| Amine Reactant | Pyromellitic Diimide Product | M.P. °C. |
|---|---|---|
| 2-Methoxyethylamine | N,N'-bis(2-methoxyethyl) | 177–178 |
| 2-Aminoethanethiol | N,N'-bis(2-mercaptoethyl) | 232–233 |
| 2-Methylthioethylamine | N,N'-bis(2-methylthioethyl) | 233–234 |
| 2-Dimethylaminoethylamine | N,N'-bis(2-dimethylamino-eth-1-yl) dihydrochloride | >300 |
| 3-Dimethylaminopropylamine | N,N'-bis(3-dimethylaminoprop-1-yl) | 186–187 |
| Ethyl glycinate | N,N'-bis(carbethoxymethyl) | 187–188 |
| N-Acetylethylenediamine | N,N'-bis(N-acetylaminoethyl) | |
| 2-Chloroethylamine | N,N'-bis(2-chloroethyl) | 208–210 |
| 2-Bromoethylamine | N,N'-bis(2-bromoethyl) | 203–204 |
| 4-Nitroaniline | N,N-bis(4-nitrophenyl) | >300 |

EXAMPLE 8

N,N'-bis(2-methylsulfinylethyl)-pyromellitic diimide

A solution containing 2.04 g. (10 mmole) of 85% m-chloroperoxybenzoic acid in 45 ml. of methylene chloride is added dropwise slowly with stirring at room temperature (23° C.) to 3.64 g. (10 mmole) of N,N'-bis(2-methylthioethyl)pyromellitic diimide in 270 ml. of 10% methanol/methylene chloride. After the addition, the mixture is stirred for 1 hour at room temperature and then concentrated to a small volume under reduced pressure. The concentrate is diluted with ethyl ether. The insolubles are collected, rinsd with ethyl ether, and dried furnishing N,N'-bis(2-methylsulfinylethyl) pyromellitic diimide.

EXAMPLE 9

N,N'-bis(2-methylsulfonylethyl)pyromellitic diimide 3.64 G. (10 mmole) of N,N'-bis(2-methylthioethyl)-pyromellitic diimide and 5.07 g. (25 mmole) of m-chloroperoxybenzoic acid in 345 ml. of glacial acetic acid are heated at 100° C. with stirring for 4 hours and then cooled in ice. The insolubles are collected, rinsed with methylene chloride and dried furnishing N,N'-bis(2-methylsulfonylethyl) pyromellitic diimide.

EXAMPLE 10

N,N'-bis(2-Aminoethyl)pyromellitic diimide

To a stirred solution of liquid ammonia, 22 ml. (1.0 mole), in 200 ml. of dimethylformamide is added portionwise 4.3 g. (10 mmole) of N,N'-bis(2-bromoethyl) pyromellitic diimide. The mixture is stirred at room temperature for 48 hours. Excess ammonia is removed by concentration under reduced pressure without heating. The concentrate is diluted with several volumes of dilute aqueous sodium bicarbonate and cooled. The insolubles are collected, rinsed with water, cold methanol and ethyl ether furnishing N,N'-bis(2-aminoethyl)-pyromellitic diimide.

EXAMPLE 11

N',N'-bis(2-methylaminoethyl)pyromellitic diimide

Following the procedure of Example 10 using 22 ml. (0.5 mole) of liquid methylamine in place of the ammonia and stirring the mixture for 16 hours provides N,N'-bis(2-methylaminoethyl) pyromellitic diimide.

EXAMPLE 12

N,N'-Symmetrical dialkanoyl and N,N'-dibenzoyl pyromellitic diimides—General procedure Pyromellitic diimide is added to a pyridine solution containing two molecular equivalents or an excess of the appropriate alkanoyl or benzoyl anhydride. This mixture is stirred at 95° C., and the product crystallizes on cooling in ice. The product is filtered, rinsed with cold pyridine, cold methanol and cold ethyl ether and is dried in vacuo at 60° C.

EXAMPLE 13

N,N'-Diacetylpyromellitic diimide

50 G. of pyromellitic diimide is heated at 95° C. for 3 hours in 150 ml. of pyridine/acetic anhydride (1:1). The product is isolated as in Example 12 furnishing 54.5 g. of N,N'-diacetylpyromellitic diimide which is recrystallized from methylene chloride/methanol (4:1) yielding 21.7 g., m.p. 259°–261° C.

EXAMPLE 14

N,N'-Dipropionylpyromellitic diimide

30 G. of pyromellitic diimide is added to a warm solution containing 300 ml. of pyridine/acetic anydride (2:1). The mixture is stirred at 95° C. for 10 minutes, cooled in an ice bath, and diluted with 300 ml. of ethyl ether. The crystals are collected, rinsed with ethyl ether and dried furnishing 42.2 g. of N,N'-dipropionylpyromellitic diimide, m.p. 230°–231° C.

EXAMPLE 15

N,N'-Dibutyrylpyromellitic diimide 30.3 G. (0.14 mole) of pyromellitic diimide is added to a solution of butyric anhydride, 66.4 g. (0.42 mole), in 1.0 l. of pyridine. The mixture is stirred at 95° C. for 30 minutes and then isolated as in Example 12 furnishing 31.3 g. of N,N'-dibutyrylpyromellitic diimide, m.p. 235°–6° C.

EXAMPLE 16

N,N,'-Dibenzoylpyromellitic diimide 21.6 G. (10 mmoles) of pyromellitic diimide is added to a solution of benzoic anhydride, 9.2 g. (40 mmole) in 40 ml. of pyridine, and the resulting mixture is stirred at 95° C. for 8 hours. The product is isolated as in Example 12 furnishing 1.5 g. of N,N'-dibenzoyl pyromellitic diimide, m.p. 310°–11° C. dec. The product is recrystallized from methylene chloride.

TABLE V

N,N'-Symmetrically Disubstituted Pyromellitic Diimides Containing Substituted N-amino Side Chains
Prepared as described in Example 6

| Amine Reactant | Pyromellitic Diimide Product | M.P. °C. |
|---|---|---|
| Unsym. dimethylhydrazine | N,N'-bis(dimethylamino) | 293–294 |
| Acethydrazide | N,N'-bis(acetylamino) | >300 |
| Butyric Acid hydrazide | N,N'-bis(butyroylamino) | >300 |
| Benzoic acid hydrazide | N,N'-bis(benzoylamino) | >300 |
| Ethyl carbazate | N,N'-bis(carbethoxyamino) | >300 |

What is claimed is:

1. A method for improving the feed efficiency of ruminant animals which comprises orally administering to a ruminant animal an effective amount of a compound having the formula:

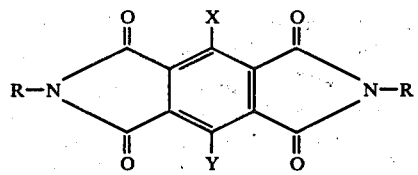

wherein each R is the same and represents hydrogen, loweralkyl, loweralkenyl, loweralkynyl, cyclopropyl, nitrophenyl; substituted loweralkyl wherein the substituent is one or two of hydroxy, hydroxyloweralkoxy, hydroxyloweralkylthio, amino, mono- or di-loweralkylamino, mono- or di-(hydroxy substituted loweralkyl)amino, loweralkanoyloxy, loweralkoxy, mercapto, loweralkylthio, loweralkylsulfinyl, loweralkylsulfonyl or loweralkoxycarbonyl; loweralkanoyl, benzoyl, diloweralkylamino, mono-substituted amino wherein the substituent is loweralkanoyl, benzoyl or loweralkanoyloxy;

X and Y are independently hydrogen, halogen or loweralkyl.

2. The method of claim 1 wherein the compound being administered to the ruminant has the structural formula of claim 1 and wherein R is hydrogen, loweralkyl, loweralkenyl, substituted loweralkyl wherein the substituents are one or two of hydroxy, amino, mono- or di-loweralkylamino, hydroxyloweralkoxy, hydroxyloweralkylthio, loweralkanoyloxy, loweralkoxy or loweralkoxycarbonyl; loweralkanoyl, diloweralkylamino or mono-substituted amino wherein the substituent is loweralkanoyl; and X and Y are hydrogen.

3. The method of claim 2 wherein the compound being administered to the ruminant has the formula wherein R is hydrogen loweralkyl, loweralkenyl, substituted loweralkyl wherein the substituent is one of hydroxy or loweralkanoyloxy; loweralkanoyl, or diloweralkylamino.

4. The method of claim 2 wherein the compound being administered to the ruminant has the formula wherein R is hydrogen or hydroxyloweralkyl.

5. The method of claim 4 wherein the compound being administered is pyromellitic diimide.

6. The method of claim 4 wherein the compound being administered is N,N'-bis(2-hydroxyethyl)pyromellitic diimide.

7. The method of claim 1 wherein the compound is administered at the rate of from 0.1 to 10 mg./kg/day.

8. The method of claim 7 wherein the compound is administered at the rate of from 0.5 to 5 mg./kg/day.

9. A composition useful for the improvement of feed efficiency in ruminants when orally administered to ruminants which comprises an inert carrier and a compound having the formula:

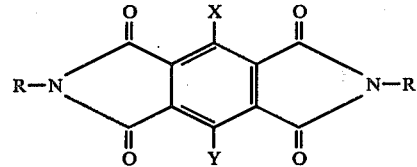

wherein each R is the same and represents hydrogen, loweralkenyl, loweralkynyl, cyclopropyl, nitrophenyl; substituted loweralkyl wherein the substituent is one or two of hydroxy, hydroxyloweralkoxy, hydroxyloweralkylthio, amino, mono- or di-loweralkylamino, mono- or di-(hydroxy substituted loweralkyl)amino, loweralkanoyloxy, loweralkoxy, mercapto, loweralkylthio, loweralkylsulfinyl, loweralkylsulfonyl or loweralkoxycarbonyl; benzoyl, diloweralkylamino, or mono-substituted amino wherein the substituent is loweralkanoyl, benzoyl or loweralkanoyloxy;

X and Y are independently hydrogen, halogen or loweralkyl.

10. The composition of claim 9 wherein the active compound of said composition has the structural formula of claim 7 wherein R is hydrogen, loweralkyl, loweralkenyl, substituted loweralkyl wherein the substituents are one or two of hydroxy, amino, mono- or di-loweralkylamino, hydroxyloweralkoxy, hydroxyloweralkylthio, loweralkanoyloxy, loweralkoxy or loweralkoxycarbonyl; diloweralkylamino or mono-substituted amino wherein the substituent is loweralkanoyl; and X and Y are hydrogen.

11. The composition of claim 10 wherein the active compound of the composition has the formula wherein R is hydrogen, loweralkyl, loweralkenyl, substituted loweralkyl wherein the substituent is one of hydroxy or loweralkanoyloxy; or diloweralkylamino.

12. The composition of claim 11 wherein the compound being administered to the ruminant has the formula wherein R is hydrogen or hydroxy loweralkyl.

13. The composition of claim 12 wherein the active compound is pyromellitic diimide.

14. The composition of claim 12 wherein the active compound is N,N'-bis-(2-hydroxyethyl)pyromellitic diimide.

15. The composition of claim 9 which is a feed premix containing from about 1 to 400 g. of active compound per pound of premix.

* * * * *